US006306403B1

United States Patent
(12) United States Patent
Donovan

(10) Patent No.: US 6,306,403 B1
(45) Date of Patent: Oct. 23, 2001

(54) METHOD FOR TREATING PARKINSON'S DISEASE WITH A BOTULINUM TOXIN

(75) Inventor: Stephen Donovan, Capistrano Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/596,306

(22) Filed: Jun. 14, 2000

(51) Int. Cl.$^7$ .......................... A61K 39/08; A61K 39/385; A01N 37/18

(52) U.S. Cl. .......................... 424/239.1; 514/2; 514/963; 424/197.11; 424/408

(58) Field of Search .......................... 424/239.1, 236.1, 424/197.11, 234.1; 514/937, 944, 2

(56) References Cited

U.S. PATENT DOCUMENTS

| | | | |
|---|---|---|---|
| 5,978,702 * | 11/1999 | Ward et al. | 607/3 |
| 5,989,545 | 11/1999 | Foster et al. . | |
| 6,094,598 * | 7/2000 | Elsberry et al. | 607/116 |
| 6,113,915 | 9/2000 | Aoki et al. . | |

FOREIGN PATENT DOCUMENTS

| | | |
|---|---|---|
| 97/20579 | 6/1997 | (WO) . |
| 00/07652 | 2/2000 | (WO) . |

OTHER PUBLICATIONS

King, D.B. , 1999, Can. J. Neurol. Sci.;26, Suppl. 2, S13–S20, p. S19.*

Jackowski, A. ,1995, Br. J. Neurosurgery, 9, 303–317, p. 303.*

Herrera, D.G. et al., 1990, Neuroscience, 35, 2, 273–281, pafe 273.*

The Merck Manual of diagnosis and therapy, 1992, Rahway, N.J., pp. 978, 1436, 1491–1495, 1500.*

Aoki, K. R., et al.; A Preclinical Comparison of the Local Muscle Weakening Efficacy, Safety, and Antigenic Potential of Botulinum Neurotoxin Serotypes A, B, and F; *Neurology* 54, Apr. 2000 (Suppl 3).

Bejjani, Boulos–Paul, et al.; Bilateral subthalmic stimulation for Parkinson's disease by using three–dimensional sterotactic magnetic resonance imaging and electrophysiological guidance; *J. Neurosurg* 92:615–625, 2000.

Berman, Robert M., et al; A Randomized Clinical Trial of Repetitive Transcranial Magnetic Stimulation in the Treatment of Major Depression; *Biological Psychiatry* 2000; 47;332–337.

Bigalke, Hans, et al.; Botulinum A Neurotoxin Inhibits Non–Cholinergic Synaptic Transmission in Mouse Spinal Cord Neurons in Culture; *Brain Research* 360(1985) 318–324 Elsevier.

Bigalke, H., et al.; Tetanus Toxin and Botulinum A Toxin Inhibit Release and Uptake of Various Transmitters, as Studied with Particulate Preparations from Rat Brain and Spinal Cord; *Naunyn–Schmiedeberg's Arch Pharmacol* (1981), 316:244–251.

Billet, Sara, et al.; Cholinergic projections to the visual thalamus and superior colliculus; *Brain Research* 847 (1999), 121–123.

Boltzmann, Ludwig; Post mortem studies in Parkinson's disease—is it possible to detect brain areas for specific syndromes?; *J Neural Transm* (1999) Suppl 56: 1–29.

Brem, Henry, et al.; Placebo–controlled trial of safety and efficacy of intraoperative controlled delivery by biodegradable polymers of chemotherapy for recurrent gliomas; *The Lancet* vol 345, Apr. 22, 1995: 1008–1012.

Brem, Henry, et al.; The safety of interstitial chemotherapy with BCNU–loaded polymer followed by radiation therapy in the treatment of newly diagnosed malignant gliomas; phase 1 trial; *Journal of Neuro–Oncology* 26: 111–123, 1995.

Brophy, B. P., et al.; Thalamotomy for Parkinsonsonian Tremor; *Stereotact Funct Neurosurg* 1997;69: 1–4.

Fung, Lawrence K., et al., Pharmacokinetics of Interstitial Delivery of Carmustine, 4–Hydroperoxycyclophosphamide, and Paclitaxel from a Biodegradable Polymer Implant in the Monkey Brain; *Cancer Research* 58, 672–684, Feb. 15, 1998.

Gary, Mary G., et al.; Evaluation of the efficacy of a bioerodible bupivacaine polymer system on antinociception and inflammatory mediator release; *Pain* 82 (1999) 49–55.

Gaspar, Laurie E., et al.; Permanent $^{125}$ Iodine Implants for Recurrent Malignant Gliomas; *Int. J. Radiation Oncology Biol Phys.* 1999, vol. 43, No. 5, 977–982.

Habermann, E.; Inhibition by tetanus and botulinum A toxin of the release of [$^3$H]noradrenaline and [$^3$H]GABA from at brain homogenate; *Experientia* 44 (1988) 224–226, Birkhauser Verlag, CH–4010 Basel/Switzerland.

Habermann, Ernst, et al.; Tetanus Toxin and Botulinum A and C Neurotoxins Inhibit Noradrenaline Release form Cultured Mouse Brain; *Journal of Neurochemistry* vol. 51, No. 2, 1988, 522–527.

Hagenah, R. et al.; Effects of Type A Botulinum Toxin on the Cholinergic Transmission at Spinal Renshaw Cells and on the Inhibitory Action at Ia Inhibitory Interneurones; *Naunyn–Schmiedeberg's Arch. Pharmacol.* 299, 267–272 (1977).

Hoffman, Ralph E., et al., Transcranial magnetic stimulation and auditory hallucinations in schizophrenia; *The Lancet* vol. 355, Mar. 25, 2000, 1073–1075.

(List continued on next page.)

*Primary Examiner*—Christine J. Saoud
*Assistant Examiner*—Olga N. Chernyshev
(74) *Attorney, Agent, or Firm*—Martin A. Voet; Robert J. Baran; Carlos A. Fisher

(57) ABSTRACT

Methods for treating a movement disorder by intracranial administration to a human patient of a therapeutically effective amount of a neurotoxin, such as a botulinum toxin type A.

17 Claims, No Drawings

OTHER PUBLICATIONS

Hoffman, Ralph E., Transcranial Magnetic Stimulation of Left Temporoparietal Cortex in Three Patients Reporting Hallucinated "Voices"; *Biol Psychiatry* 1999; 46:130–132.

Johnson, Eric A., Biomedical Aspects of Botulinum Toxin; *J. Toxicol Toxin Rev.* Feb. 18, 1999; 18(1):1–15.

Jung, H. H., et al.; Expression of Neurotransmitter Genes in Rat Spinal Motoneurons After Chemodenervation With Botulinum Toxin; *Neuroscience* vol. 78, No. 2, 469–479, 1997.

Koller, William C., et al.; Surgical treatment of Parkinson's disease; *Journal of the Neurological Sciences* 167 (1999) 1–10.

Larsen, hans R.; Parkinson's Disease: Is Victory in Sight?; *International Health News* 1977, Internet: health@pinc.com. 7 pages.

Marjama–Lyons, Jill, et al.; Tremor–Predominant Parkinson's Disease, Approaches To Treatment; *Drugs & Aging* Apr.: 2000 16(4): 273–278.

Nadeau, Stephen E.; Parkinson's Disease; *JAGS* 45:233–240, 1997.

Nowinski, Wieslaw. L., et al.; Computer–Aided Sterotactic Functional Neurosurgery Enhanced by the Use of the Multiple Brain Atlas Database; *IEEE Transactions On Medical Imaging* vol. 19, No. 1 Jan. 2000, 62–69.

Oakman, S. A., et al.; Characterization of the Extent of Pontomesencephalic Cholinergic Neurons' Projections to the Thalamus: Comparison with Projections to Midbrain Dopaminergic Groups; *Neuroscience* vol. 94, No. 2, 529–547, 1999.

Pearce, Bruce L., et al.; Pharmacologic Characterization of Botulinum Toxin for Basic Science and Medicine; *Toxicom* vol. 35, No. 9, 1373–1412, 1997.

Perry, Elaine, et al.; Acetylcholine in mind; a neurotransmitter correlate of consciousness?; *TINS* vol. 22, No. 6, 1999, 273–280.

Playfer, JR; Parkinson's disease; *Postgrad Med J* 1997; 73: 257–264.

Powell, Elizabeth M., et al.; Controlled release of nerve growth factor from a polymeric implant; *Brain Research* 515 (1990) 309–311, Elsevier.

Rao, Jyoti K., et al.; Implantable controlled delivery systems for proteins based on collagen—pHEMA hydrogels; *Biomaterials* 1994, vol. 15, No. 5, pp. 383–389.

Rico, Beatriz, et al.; A population of cholinergic neurons is present in the macaque monkey thalamus; *European Journal of Neuroscience* vol. 10, pp. 2346–23352, 1998.

Sanchez–Prieto, Jose, et al.; Botulinum toxin A blocks glutamate exocytosis from guinea–pig cerebral cortical synaptosomes; *Eur. J. Biochem.* 165:675–681 (1987) Febs 1987.

Schafer, M. K.–H., et al.; Cholinergic Neurons and Terminal Fields Revealed by Immunohistochemistry for the Vesicular Acetylcholine Transporter. 1. Central Nervous System; *Neuroscience* vol. 84, No. 2, pp. 331–359, 1998.

Scharfen, Cindy O., et al.; High Activity Iodine–125 Interstitial Impalnt for Gliomas; *Int. J. Radiation Oncology Biol. Phys.* vol. 24, pp. 583–591.

Schuurman, Richard P., et al.; A Comparison of Continuous Thalamic Stimulation and Thalamotomy for Suppression of Severe Tremor; *The New England Journal of Medicine* vol. 342, No. 7, pp. 461–468, Feb. 17, 2000.

Speelman, J. D., et al.; Thalamic Surgery and Tremor; *Movement Disorders* vol. 13, Suppl. 3, 1998, pp. 103–106.

Williamson, Lura C., et al.; Clostridial Neurotoxins and Substrate Proteolysis in Intact Neurons; *The Journal of Biological Chemistry* vol. 271, No. 13, Mar. 29, pp. 7694–7699, 1996.

U.S. application No. 09/587,250 Donovan et al., filed Jun. 2, 2000.

Aoki, R.; Preclinical Update on BOTOX® (botulinum toxin type A)–purified neurotoxin complex relative to other botulinum neurotoxin preparation; *European Journal of Neurology,* vol. 6 (supp 4) 1999; pp. S3–S10.

Aoki, R.; Botulinum toxin type A in the treatment of focal, axillary and palmar hyperhidrosis and other hyperhidrotic conditions; *European Journal of Neurology,* vol. 6 (supp 4), 1999; pp. S111–S115.

Bellazza, D. et al.; Stereotactic Interstital Brachytherapy; *Textbook of Stereotactic and Functional Neurosurgery;* Chapter 66; pp. 577–580, 1976.

Boyd R.S. et al., The effect of botulinum neurotoxin–B on insulin release from a β–cell line, Mov Disord, 10(3):376:1995.

Boyd R.S. et al., The insulin secreting β–cell line, HIT–15, contains SNAP–25 which is a target for botulinum neurotoxin–A, both published at Mov Disord, 10(3):376:1995.

Jankovic, J. et al; Therapy with Botulinum Toxin; New York, 1994; p. 150.

Jankovic, J. et al.; Therapy with Botulinum Toxin; New York, 1994; p. 5.

Fauci, A. et al; Harrison's Principles of Internal Medicine; $14^{th}$ Ed; 1998, p. 2321.

Gonelle–Gispert et al.; Snap–25a and–25b isoforms are both expressed in insulin–secreting cells and can function in insulin secretion; *Biochemical Society;* (1999); 339; pp. 159–165.

Jellinger, K.A.; Post mortem studies in Parkinson's disease—it is possible to detect brain areas for specific symptoms; *J. Nerual Transm* (suppl) 56; 1999; pp. 1–29.

Moyer, E. et al; Botulinum Toxin Type B; Experimental and Clinical Experience; *Therapy with Botulinum Toxin,* edited by Jankovic, J. et al.; pp. 71–85 (1994), New York.

Ragona, R. et al.; Management of partoid sialocele with botulinum toxin; *The Laryngoscope;* vol. 109;Philadelphia; 1999; pp. 1344–1346.

Shantz, E. et al.; Properties and sue of botulinum toxin and other microbial neurotoxins in medicine; *Microbiological Reviews;* vol. 56, No. 1; Mar. 1992; pp. 80–99.

Singh, B.; Critical Aspects of Bacterial Protein toxins; *Natural Toxins II;* Plenum Press, New York, 1996; pp. 63–84.

Steriade, M. et al; Parallel activation of thalamic and cortical neurons by brainstem and basal forebrain cholinergic systems; *Brain Cholinergic Systems;* Oxford University Press; 1990; pp. 1–64.

Stone, T. et al.; CNS Neurotransmitters and Neuromodulators Acetylcholine; New York; 1995; p. 16.

Tasker, R.; Surgical Treatment of the Dystonias; *Textbook of Stereotactic and Functional Neurosurgery;* Chapter 105; pp. 1015–1032, McGraw–Hill (1998).

Tracey, D. et al; Neurotransmitters in the human brain; Plenum Press, New York; 1995; pp. 136–139.

* cited by examiner

METHOD FOR TREATING PARKINSON'S DISEASE WITH A BOTULINUM TOXIN

BACKGROUND

The present invention relates to methods for treating movement disorders. In particular, the present invention relates to methods for treating movement disorders by intracranial administration of a neurotoxin.

Movement Disorders

A movement disorder is a neurological disturbance that involves one or more muscles or muscle groups. Movement disorders include Parkinson's disease, Huntington's Chorea, progressive supranuclear palsy, Wilson's disease, Tourette's syndrome, epilepsy, and various chronic tremors, tics and dystonias. Different clinically observed movement disorders can be traced to the same or similar areas of the brain. For example, abnormalities of basal ganglia (a large cluster of cells deep in the hemispheres of the brain) are postulated as a causative factor in diverse movement disorders.

Tremors are characterized by abnormal, involuntary movements. An essential tremor is maximal when the body part afflicted (often an arm or hand) is being used, for example when attempts at writing or fine coordinated hand movements are made. Typical chemotherapy is use of the drug propranolol (Inderal) which has the side effects of low blood pressure and heart rate changes. A resting tremor is common in Parkinson's disease and in syndromes with Parkinsonian features. A resting tremor is maximal when the extremities are at rest. Often, when a patient attempts fine movement, such as reaching for a cup, the tremor subsides. Systemic anticholinergic medications have been used with some success.

Dystonias are involuntary movement disorders characterized by continued muscular contractions which can result in twisted contorted postures involving the body or limbs. Causes of dystonia include biochemical abnormalities, degenerative disorders, psychiatric dysfunction, toxins, drugs and central trauma. Thalamotomy and/or subthalamotomy or campotomy are currently the preferred neurosurgical procedures to treat dystonia, and are carried out with techniques and brain targets similar to the surgical treatment of Parkinson's disease. Tasker R., *Surgical Treatment of the Dystonias*, chapter 105, pages 1015–1032, in Gildenberg P. L. et al., *Textbook of Stereotactic and Functional Neurosurgery,* McGraw-Hill (1998).

Particular dystonias can include spasmodic torticollis, blepharospasm and writer's cramp. Spasmodic torticollis is a syndrome that usually affects adults, and involves the involuntary turning of the neck to one side. Some individuals may not even notice initially that the head and neck are turned. Blepharospasm is an involuntary movement which involves intermittent forceful closure of the eyelids. Writers cramp is a cramping abnormal posture which develops when one is writing, or performing other actions with the hands. Symptoms may progress to involve the arm and shoulder.

Tic disorders (including Tourette's) are usually very rapid, short lived stereotyped repeated movements. The more common tics involve the motor systems, or are vocal in nature. Motor tics often involve the eyelids, eyebrows or other facial muscles, as well as the upper limbs. Vocal tics may involve grunting, throat clearing, coughing or cursing. Individuals with tic disorders will often describe a strong urge to perform the particular tic, and may actually feel a strong sense of pressure building up inside of them if the action is not performed. For example, a motor tic that may involve the abrupt movement of one of the arms may be controllable for a short period of time if the affected person sits on his hands; however, the almost irresistible urge to do the action often takes over and result in the tic action.

Tourette's syndrome is a tic disorder which often begins in childhood or adolescence and is much more common in males. There are both multiple motor tics, as well as vocal tics present. The tics often change from involvement of one body part to another, and the disease often gets better and worse intermittently, with periods of almost minimal activity, and other times when some patients have difficulty functioning. Other neurobehavioral difficulties often accompany the syndrome. These include attention deficit hyperactivity disorder (ADHD) and obsessive-compulsive disorder. Treatment of most tic disorders employs the use of medications that decrease the amount of dopamine in the brain, such as dopamine antagonists. Unfortunately these drugs are associated with side effects such as other movement disorders, including Parkinsonism (stiffness, slow movement and tremors). In addition to Tourette's syndrome, tics may be associated with head injury, carbon monoxide poisoning, stroke, drug use and mental retardation.

Progressive supranuclear palsy is a movement disorder in which patients have significant difficulty moving their eyes vertically (up and down) initially, followed by all eye movements become limited (ophthalmoplegia). Patients can also develop dementia, rigidity, bradykinesia (slow movements) and a propensity for falls.

Huntington's chorea is a genetically inherited disorder that has both neurological and psychiatric features. Most cases develop when people are in their forties or fifties, but early and late onset is also possible. The disease may begin with either the neurological or mental status changes. The neurological symptoms may vary, but include chorea. Chorea (derived from a Greek word meaning, "to dance") is a series of movements that is dance-like, jerky, brief, and moves from one part of the body to another. Clumsiness, fidgetiness and jumpiness may also occur. Facial movements, especially around the jaw, may occur. There is often difficulty with walking and posture. The psychiatric symptoms may present as paranoia, confusion, or personality changes. As the disease progresses, a significant dementia develops. MRI brain imaging may show atrophy (shrinkage) of a portion of the basal ganglia (involved in movement) that is known as the caudate nucleus.

Wilson's disease is a disorder that involves the nervous system and liver function. The neurological problems include tremors, incoordination, falling, slurred speech, stiffness and seizures. Psychiatric problems can occur and patients can develop severe liver damage if this affliction is untreated. Elevated copper and ceruloplasmin levels are diagnostic.

Unfortunately, a movement disorder, including those set forth above, can become resistant to drug therapy. Drug resistant tremors can include resting tremors, such as can occur in Parkinson's disease, and action tremors, such as essential tremor, multiple sclerosis tremors, post traumatic tremors, post hemiplegic tremors (post stroke spasticity), tremors associated with neuropathy, writing tremors and epilepsy.

Parkinson's Disease

Parkinson's disease is a movement disorder of increasing occurrence in aging populations. Parkinson's disease is a common disabling disease of old age affecting about one percent of the population over the age of 60 in the United States. The incidence of Parkinson's disease increases with age and the cumulative lifetime risk of an individual developing the disease is about 1 in 40. Symptoms include pronounced tremor of the extremities, bradykinesia, rigidity and postural change. A perceived pathophysiological cause of Parkinson's disease is progressive destruction of dopamine producing cells in the basal ganglia which comprise the pars compartum of the substantia nigra, a basal nuclei located in the brain stem. Loss of dopamineric neurons results in a relative excess of acetylcholine. Jellinger, K. A., *Post Mortem Studies in Parkinson's Disease—Is It Possible to Detect Brain Areas For Specific Symptoms?*, J Neural Transm 56 (Supp);1–29:1999.

Parkinson's disease is a progressive disorder which can begin with mild limb stiffness and infrequent tremors and progress over a period of ten or more years to frequent tremors and memory impairment, to uncontrollable tremors and dementia.

Drugs used to treat Parkinson's disease include L-dopa, selegiline, apomorphine and anticholinergics. L-dopa (levodihydroxy-phenylalanine) (sinemet) is a dopamine precursor which can cross the blood-brain barrier and be converted to dopamine in the brain. Unfortunately, L-dopa has a short half life in the body and it is typical after long use (i.e. after about 4–5 years) for the effect of L-dopa to become sporadic and unpredictable, resulting in fluctuations in motor function, dyskinesias and psychiatric side effects. Additionally, L-dopa can cause B vitamin deficiencies to arise.

Selegiline (Deprenyl, Eldepryl) has been used as an alternative to L-dopa, and acts by reducing the breakdown of dopamine in the brain. Unfortunately, Selegiline becomes ineffective after about nine months of use. Apomorphine, a dopamine receptor agonist, has been used to treat Parkinson's disease, although is causes severe vomiting when used on its own, as well as skin reactions, infection, drowsiness and some psychiatric side effects.

Systemically administered anticholinergic drugs (such as benzhexol and orphenedrine) have also been used to treat Parkinson's disease and act by reducing the amount of acetylcholine produced in the brain and thereby redress the dopamine/acetylcholine imbalance present in Parkinson's disease. Unfortunately, about 70% of patients taking systemically administered anticholinergics develop serious neuropsychiatric side effects, including hallucinations, as well as dyskinetic movements, and other effects resulting from wide anticholinergic distribution, including vision effects, difficulty swallowing, dry mouth and urine retention. See e.g. Playfer, J. R., *Parkinson's Disease*, Postgrad Med J, 73;257–264:1997 and Nadeau, S. E., *Parkinson's Disease*, J Am Ger Soc, 45;233–240:1997.

Before the introduction of L-dopa in 1969, stereotactic surgery offered one of the few effective treatments for Parkinson's disease. The significant known deficiencies and drawbacks associated with therapeutic drugs to treat Parkinson's disease, including the long term limitations of L-dopa therapy have led to renewed interest in neurosurgical intervention. Unilateral stereotactic thalamotomy has proven to be effective for controlling contralateral tremor and rigidity, but carries a risk of hemiparesis. Bilateral thalamotomy carries an increased risk of speech and swallowing disorders resulting. Stereotactic pallidotomy, surgical ablation of part of the globus pallidus (a basal ganglia), has also be used with some success. Aside from surgical resection, high frequency stimulating electrodes placed in the ventral intermedialis nucleus has been found to suppress abnormal movements in some cases. A variety of techniques exist to permit precise location of a probe, including computed tomography and magnetic resonance imaging. Unfortunately, the akinesia, speech and gait disorder symptoms of Parkinson's disease are little helped by these surgical procedures, all of which result in destructive brain lesions.

Epilepsy

A seizure is a paroxysmal event due to abnormal, excessive, hypersynchronous discharges from an aggregate of central nervous system neurons. Epilepsy describes a condition in which a person has recurrent seizures due to a chronic, underlying process. Among the many causes of epilepsy there are various epilepsy syndromes in which the clinical and pathologic characteristics are distinctive and suggest a specific underlying etiology. The prevalence of epilepsy has been estimated at 5 to 10 people per 1000 population. Severe, penetrating head trauma is associated with up to a 50% risk of leading to epilepsy. Other causes of epilepsy include stroke, infection and genetic susceptibility.

Antiepileptic drug therapy is the mainstay of treatment for most patients with epilepsy and a variety of drugs have been used. See e.g., Fauci, A. S. et al., *Harrison's Principles of Internal Medicine*, McGraw-Hill, $14^{th}$ Edition (1998), page 2321. Twenty percent of patients with epilepsy are resistant to drug therapy despite efforts to find an effective combination of antiepileptic drugs. Surgery can then be an option. Video-EEC monitoring can be used to define the anatomic location of the seizure focus and to correlate the abnormal electrophysiologic activity with behavioral manifestations of the seizure. Routine scalp or scalp-sphenoidal recordings are usually sufficient for localization. A high resolution MRI scan is routinely used to identify structural lesions. Functional Imaging studies such as SPECT and PET are adjunctive tests that can help verify the localization of an apparent epileptogenic region with an anatomic abnormality. Once the presumed location of the seizure onset is identified, additional studies, including neuropsychological testing and the intracarotid amobarbital test (Wada's test) can be used to assess language and memory localization and to determine the possible functional consequences of surgical removal of the epileptogenic region. In some cases, the exact extent of the resection to be undertaken can be determined by performing cortical mapping at the time of the surgical procedure. This involves electrophysiologic recordings and cortical stimulation of the awake patient to identify the extent of epileptiform disturbances and the function of the cortical regions in questions.

The most common surgical procedure for patients with temporal lobe epilepsy involves resection of the anteromedial temporal lobe (temporal lobectomy) or a more limited removal of the underlying hippocampus and amygdala. Focal seizures arising from extratemporal regions may be suppressed by a focal neocortical resection. Unfortunately, about 5% of patients can still develop clinically significant complications from surgery and about 30% of patients treated with temporal lobectomy will still have seizures.

Focal epilepsy can involve almost any part of the brain and usually results from a localized lesion of functional abnormality. One type of focal epilepsy is the psychomotor seizure. Current therapy includes use of an EEG to localize abnormal spiking waves originating in areas of organic brain disease that predispose to focal epileptic attacks, followed by surgical excision of the focus to prevent future attacks.

Brain Motor Systems

Several areas of the cerebrum influence motor activity. Thus, lesion to the motor cortex of the cerebrum, as can result from stoke, can remove inhibition of vestibular and reticular brain stem nuclei, which then become spontaneously active and cause spasm of muscles influenced by, the now disinhibited, lower brain areas.

An accessory motor system of the cerebrum is the basal ganglia. The basal ganglia receives most input from and sends most of its signals back to the cortex. The basal ganglia include the caudate nucleus, putamen, globus pallidus, substantia nigra (which includes the pars compacta) and subthalamic nucleus. Because abnormal signals from the basal ganglia to the motor cortex cause most of the abnormalities in Parkinson's disease, attempts have been made to treat Parkinson's disease by blocking these signals. Thus lesions have been made in the ventrolateral and ventroanterior nuclei of the thalamus to block the feedback circuit from the basal ganglia to the cortex. Additionally, pallidotomy, the surgical ablation of part of the globus pallidus, has been used to effectively treat the motor disorders of Parkinson's disease.

Surgical intervention is believed to assist by interrupting a motoric pathway which, due to a dopaminergic deficiency, had pathologically inhibited the thalamus. The inhibited thalamus in turn understimulates cortical neuronal networks responsible for generating movement. Hence, surgery removes the thalamic inhibition and has been used in the treatment of pharmacoresistant movement disorders. Speelman, J. D., et al., *Thalamic Surgery and Tremor*, Mov Dis 13(3);103–106:1998.

Intracranial lesions for the treatment of tremor and other parkinsonian symptoms have been made to the globus pallidus and the ansa lenticularis. Long term results of pallidotomy have sometimes been disappointing. Positive results for the surgical arrest of tremor have been obtained by lesioning the following thalamic nuclei: (1) the ventrointermedius (Vim) or ventral lateral posterior (VLp) nucleus; (2) ventrooralis anterior (Voa) nucleus (Voa and Vop have been collectively termed the ventral lateral anterior nucleus (VLa)); (3) ventrooralis posterior (Vop) nucleus; (4) subthalamic nuclei (campotomy), and; (5) CM-Pf thalamic nuclei. Generally, the ventrolateral thalamus has been the surgical target of choice in the treatment of Parkinson's disease and other systemically administered, drug resistant tremors. Brophy, B. P., et al., *Thalamotomy for Parkinsonian Tremor*, Stereotact Funct Neurosurg, 69;1–4:1997. Thalamic excitation of the cortex is necessary for almost all cortical activity.

Stereotactic surgery (assisted by neuroimaging and electrophysiologic recordings) has been used in the management of advanced, pharmacoresistant Parkinson's disease, targeting hyperactive globus pallidus and subthalamic nuclei. An electrode or a probe is placed into the brain using a brain atlas for reference with assistance from brain imaging by computer tomography or magnetic resonance imaging. Lesions in different parts of the pallidum (i.e. posteroventral pallidum), basal ganglia, thalamus and subthalamic nuclei have been carried out to treat motor disorders of Parkinson's disease. Unfortunately, surgical brain lesions create a risk of impairment to speech, visual and cognitive brain areas. Neurotransplantation shows promise but requires further investigation. Additionally, deep brain stimulation using electrodes for the suppression of tremor using can create problems due to wire erosion, lead friction, infection of the implantable pulse generator, malfunction of the implantable pulse generator, electrical shock and lead migration. Other complications due to electrode stimulation can include dysarthria, disequilibrium, paresis and gait disorder. See e.g. Koller, W. C. et al., *Surgical Treatment of Parkinson's Disease*, J Neurol Sci 167;1–10:1999, and Schuurman P. R., et al., *A Comparison of Continuous Thalamic Stimulation and Thalamotomy for Suppression of Severe Tremor*, NEJM 342(7);461–468:2000.

Aside from surgical ablation or stimulation, external radiotherapy (Gamma Knife Radiosurgery) has also been used to a limited extent for the treatment of drug resistant parkinsonian tremors. Drawbacks with this procedure are that the reduction in tremor is delayed by between one week and eight months after the radiosurgery, and that long term benefits as well as radiation side effects are currently unknown.

As set forth, treatment of parkinsonian tremor and other movement disorders has been carried out by thalamotomy and/or interruption of pallidofugal fibers in the subthalamic region and pallidotomy has also been used. Current concepts of basal ganglia circuitry propose that the loss of striatal dopamine in Parkinson's disease leads to overactivity of the striatal projection to the lateral segment of the globus pallidus. The resulting decrease in lateral pallidal activity results in disinhibition of the subthalamic nucleus, its main projection site. Increased subthalamic activity in turn causes overactivity of the internal segment of the globus pallidus, which projects to the pedunculopontine nucleus (PPN) and the ventrolateral (VL) thalamus. Thus, overactivity in the subthalamic nucleus and internal pallidum produces the parkinsonian symptoms of tremor, bradykinesia and hypokinesia through projections to the PPN and VL thalamus. Lesion in the subthalamic nucleus and the results of pallidotomy, particularly posteroventral pallidotomy, have permitted effective treatment of akinesia in parkinsonian patients.

*Botulinum* Toxin

The genus Clostridium has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1996) (where the stated $LD_{50}$ of *botulinum* toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials)

Seven immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. Moyer E et al., *Botulinum Toxin Type B: Experimental and Clinical Experience*, being chapter 6, pages 71–85 of "Therapy With Botulinum Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype $C_1$ was originally thought to cleave syntaxin, but was found to cleave syntaxin and SNAP-25. Each of the *botulinum* toxins specifically cleaves a different bond, except *botulinum* toxin type B (and tetanus toxin) which cleave the same bond.

*Botulinum* toxins have been used in clinical settings for the treatment of neuromuscular disorders characterized by hyperactive skeletal muscles. A *botulinum* toxin type A complex has been approved by the U.S. Food and Drug Administration for the treatment of blepharospasm, strabismus and hemifacial spasm. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type C, has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. Gonelle-Gispert, C., et al., *SNAP-25a and -25b isoforms are both expressed in insulin-secreting cells and can function in insulin secretion*, Biochem J. 1;339 (pt 1):159–65:1999, and Boyd R. S. et al., *The effect of botulinum neurotoxin-B on insulin release from a β-cell line*, and Boyd R. S. et al., *The insulin secreting β-cell line, HIT-15, contains SNAP-25* which is a target for *botulinum neurotoxin-A*, both published at *Mov Disord,* 10(3):376:1995 (pancreatic islet B cells contains at least SNAP-25 and synaptobrevin).

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. *Botulinum* toxin types B and $C_1$ is apparently produced as only a 700 kD or 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522–527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675–681:1987. Thus, when adequate concentrations are used, stimulus-evoked release of most neurotransmitters is blocked by *botulinum* toxin. See e.g. Pearce, L. B., *Pharmacologic Characterization of Botulinum Toxin For Basic Science and Medicine*, Toxicon 35(9);1373–1412 at 1393; Bigalke H., et al., *Botulinum A Neurotoxin Inhibits Non-Cholinergic Synaptic Transmission in Mouse Spinal Cord Neurons in Culture*, Brain Research 360;318–324:1985; Habermann E., *Inhibition by Tetanus and Botulinum A Toxin of the release of [$^3$H]Noradrenaline and [$^3$H]GABA From Rat Brain Homogenate*, Experientia 44;224–226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244–251:1981, and; Jankovic J. et al., *Therapy With Botulinum Toxin*, Marcel Dekker, Inc., (1994), page 5.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geqq 3\times10^7$ U/mg, an $A_{260}/A_{278}$ of less than 0.60 and a distinct pattern of banding on gel electrophoresis. The known Schantz process can be used to obtain crystalline *botulinum* toxin type A, as set forth in Schantz, E. J., et al, *Properties and use of Botulinum toxin and Other Microbial Neurotoxins in Medicine*, Microbiol Rev. 56;80–99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of $1–2\times10^8$ $LD_{50}$ U/mg or greater; purified *botulinum* toxin type B with an approximately 156 kD molecular weight with a specific potency of $1–2\times10^8$ $LD_{50}$ U/mg or greater, and; purified *botulinum* toxin type F with an approximately 155 kD molecular weight with a specific potency of $1–2\times10^7$ $LD_{50}$ U/mg or greater.

*Botulinum* toxins and/or *botulinum* toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Pure *botulinum* toxin is so labile that it is generally not used to prepare a pharmaceutical composition. Furthermore, the *botulinum* toxin complexes, such a the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology,* 48:249–53:1997.

It has been reported that *botulinum* toxin type A has been used in clinical settings as follows:

(1) about 75–125 units of BOTOX® per intramuscular injection (multiple muscles) to treat cervical dystonia;

(2)5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patient's with Parkinson's disease, although it has been reported that results have not been impressive. Mariama-Lyons, J., et al., *Tremor-Predominant Parkinson's Disease*, Drugs & Aging 16(4) ;273–278:2000.

It is known that *botulinum* toxin type A can have an efficacy for up to 12 months (Naumann M., et al, *Botulinum* toxin type A in the treatment of focal, axillary and palmar hyperhidrosis and other hyperhidrotic conditions, European J. Neurology 6 (Supp 4): S111–S115:1999), and in some circumstances for as long as 27 months. Ragona, R. M., et al., *Management of parotid sialocele with botulinum* toxin. The Laryngoscope 109:1344–1346:1999. However, the usual duration of an intramuscular injection of Botox® is typically about 3 to 4 months.

The success of *botulinum* toxin type A to treat a variety of clinical conditions has led to interest in other *botulinum* toxin serotypes. A study of two commercially available botulinum type A preparations (BOTOX® and DYSPORT®) and preparations of *botulinum* toxins type B and F (both obtained from Wako Chemicals, Japan) has been carried out to determine local muscle weakening efficacy, safety and antigenic potential. *Botulinum* toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or *botulinum* toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for *botulinum* toxin type B or 0.15 ng/kg for BOTOX®). Peak muscle weakness and duration were dose related for all serotypes. DAS $ED_{50}$ values (units/kg) were as follows: BOTOX®: 6.7, DYSPORT®: 24.7, *botulinum* toxin type B: 27.0 to 244.0, *botulinum* toxin type F: 4.3. BOTOX® had a longer duration of action than *botulinum* toxin type B or *botulinum* toxin type F. Therapeutic index values were as follows: BOTOX®: 10.5, DYSPORT®: 6.3, *botulinum* toxin type B: 3.2. Water consumption was greater in mice injected with *botulinum* toxin type B than with BOTOX®, although *botulinum* toxin type B was less effective at weakening muscles. After four months of injections 2 of 4 (where treated with 1.5 ng/kg) and 4 of 4 (where treated with 6.5 ng/kg) rabbits developed antibodies against *botulinum* toxin type B. In a separate study, 0 of 9 BOTOX® treated rabbits demonstrated antibodies against *botulinum* toxin type A. DAS results indicate relative peak potencies of *botulinum* toxin type A being equal to *botulinum* toxin type F, and *botulinum* toxin type F being greater than *botulinum* toxin type B. With regard to duration of effect, *botulinum* toxin type A was greater than *botulinum* toxin type B, and *botulinum* toxin type B duration of effect was greater than *botulinum* toxin type F. As shown by the therapeutic index values, the two commercial preparations of *botulinum* toxin type A (BOTOX® and DYSPORT®) are different. The increased water consumption behavior observed following hind limb injection of *botulinum* toxin type B indicates that clinically significant amounts of this serotype entered the murine systemic circulation. The results also indicate that in order to achieve efficacy comparable to *botulinum* toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of *botulinum* toxin type B. Aoki, K. R., *Preclinical update on BOTOX(botulinum toxin type A)-purified neurotoxin complex relative to other botulinum neurotoxin preparations*, Eur J Neurol November 1999;6(Suppl 4):S3–S10.

In addition to having pharmacologic actions at the peripheral location, *botulinum* toxins may also have inhibitory effects in the central nervous system. Work by Weigand et al, ([125]*I-labelled botulinum A neurotoxin:pharmacokinetics in cats after intramuscular injection*, Nauny-Schmiedeberg's Arch. Pharmacol. 1976; 292, 161–165), and Habermann, ([125]*I-labelled Neurotoxin from clostridium botulinum A:preperation, binding to synaptosomes and ascent to the spinal cord*, Nauny-Schmiedeberg's Arch. Pharmacol. 1974; 281, 47–56) showed that *botulinum* toxin is able to ascend to the spinal area by retrograde transport. As such, a *botulinum* toxin injected at a peripheral location, for example intramuscularly, may be retrograde transported to the spinal cord.

U.S. Pat. No. 5,989,545 discloses that a modified clostridial neurotoxin or fragment thereof, preferably a *botulinum* toxin, chemically conjugated or recombinantly fused to a particular targeting moiety can be used to treat pain by administration of the agent to the spinal cord.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic, as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

Cholinergic Brain Systems

Cholinergic influence of both the motor and visual thalamus originates from both the brainstem and the basal forebrain. See e.g. Billet S., et al., *Cholinergic Projections to the Visual Thalamus and Superior Colliculus*, Brain Res. 847;121–123:1999 and Oakman, S. A. et al., *Characterization of the Extent of Pontomesencephalic Cholinergic Neurons' projections to the Thalamus: Comparison with Projections to Midbrain Dopaminergic Groups*, Neurosci 94(2); 529–547;1999. Thus, it is known based on histochemical studies using acetylcholinesterase (AchE) staining and retrograde tracing with choline acetyltransferase (ChAT) immunochemistry that there can be ascending cholinergic stimulation by the brainstem of thalamic neurons. Steriade M. et al., *Brain Cholinergic Systems*, Oxford University Press (1990), chapter 1. Indeed, many thalamic nuclei receive dense cholinergic innervation from brainstem reticular formations. Ibid, page 167. Known brainstem cholinergic cell groups are located within: (1) the rostral pons at what is termed a Ch5 location, which is located within the central tegmental field around the brachium conjunctivum, forming a pedunculopontine tegmental nucleus, and; (2) the caudal part of the midbrain, at what is termed a Ch6 location, the laterodorsal tegmental nucleus, which is embedded in the periaqueductal and periventricular gray matter. The Ch5 and Ch6 cell groups can consist almost exclusively of cholinergic neurons and together form the pontine cholinergic system. The Ch5–Ch6 cholinergic groups provide direct ascending projections that terminate in a number of target structure in the midbrain, diencephalon and telencephalon, including the superior colliculus, anterior pretectal area, interstitial magnocellular nucleus of the posterior commissure, lateral habenular nucleus, thalamus, magnocellular preoptic nucleus, lateral mammillary nucleus, basal forebrain, olfactory bulb, medial prefrontal cortex and pontine nuclei. Stone T. W., *CNS Neurotransmitters and Neuromodulators: Acetyicholine*, CRC Press (1995), page 16. See also Schafer M. K.-H. et al., *Cholinergic Neurons and*

*Terminal Fields Revealed by Immunochemistry for the Vesicular Acetylcholine Transporter. I. Central Nervous System*, Neuroscience, 84(2);331–359:1998. Three dimensional localization of Ch1–8 cholinergic nuclei have been mapped in humans. See e.g. Tracey, D. J., et al., *Neurotransmitters in the Human Brain,* Plenum Press (1995), pages 136–139.

Additionally, the basal forebrain (proencephalon) provides cholinergic innervation of the dorsal thalamus, as well as to the neocortex, hippocampus, amygdala and olfactory bulb. See e.g. Steridae, page 136–136, supra. Basal forebrain areas where the great proportion of neurons are cholinergic include the medial septal nucleus (Ch1), the vertical branches of the diagonal band nuclei (Ch2), the horizontal branches of the diagonal band nuclei (Ch3), and the magnocellular nucleus basalis (Ch4), which is located dorsolaterally to the Ch3 cell group. Ch1 and Ch2 provide the major component of cholinergic projection to the hippocampus. The cells in the Ch3 sector project to the olfactory bulb.

Furthermore, cholinergic neurons are present in the thalamus. Rico, B. et al., *A Population of Cholinergic Neurons is Present in the Macaque Monkey Thalamus, Eur J Neurosci,* 10;2346–2352: 1998.

Abnormalities in the brain's cholinergic system have been consistently identified in a variety of neuropsychiatric disorders including Alzheimer's disease, Parkinson's disease and dementia with Lewy bodies. Thus, in Alzheimer's disease there is hypoactivity of cholinergic projections to the hippocampus and cortex. In individuals with dementia with Lewy bodies extensive neocortical cholinergic deficits are believed to exist and in Parkinson's disease there is a loss of pedunculopontine cholinergic neurons. Notably, in vivo imaging of cholinergic activity in the human brain has been reported. Perry, et al., *Acetylcholine in Mind: a Neurotransmitter Correlate of Consciousness?*, TINS 22(6); 273–280:1999.

What is needed therefore is a method for effectively treating a movement disorder by administration of a pharmaceutical which has the characteristics of long duration of activity, low rates of diffusion out of a chosen intracranial target tissue where administered, and nominal systemic effects at therapeutic dose levels.

SUMMARY

The present invention meets this need and provides methods for effectively treating a movement disorder by intracranial administration of a neurotoxin which has the characteristics of long duration of activity, low rates of diffusion out of an intracranial site where administered and insignificant systemic effects at therapeutic dose levels.

The following definitions apply herein:

"About" means approximately or nearly and in the context of a numerical value or range set forth herein means ±10% of the numerical value or range recited or claimed.

"Biological activity" includes, with regard to a neurotoxin, the ability to influence synthesis, exocytosis, receptor binding and/or uptake of a neurotransmitter, such as acetylcholine, or of an endocrine or exocrine secretory product, such as insulin or pancreatic juice, respectively.

"Local administration" means direct administration of a pharmaceutical at or to the vicinity of a site on or within an animal body, at which site a biological effect of the pharmaceutical is desired. Local administration excludes systemic routes of administration, such as intravenous or oral administration.

"Neurotoxin" means a biologically active molecule with a specific affinity for a neuronal cell surface receptor. Neurotoxin includes Clostridial toxins both as pure toxin and as complexed with one to more non-toxin, toxin associated proteins "Intracranial" means within the cranium or at or near the dorsal end of the spinal cord and includes the medulla, brain stem, pons, cerebellum and cerebrum.

A method for treating a movement disorder within the scope of the present invention can be by intracranial administration of a neurotoxin to a patient to thereby alleviate a symptom of the movement disorder. The neurotoxin is made by a bacterium selected from the group consisting of *Clostridium botulinum, Clostridium butyricum* and *Clostridium beratti*, or can be expressed by a suitable host (i.e. a recombinantly altered *E. coli*) which encodes for a neurotoxin made by *Clostridium botulinum, Clostridium butyricum* or *Clostridium beratti*. Preferably, the neurotoxin is a *botulinum* toxin, such as a *botulinum* toxin type A, B, $C_1$, D, E, F and G.

The neurotoxin can be administered to various brain areas for therapeutic treatment of a movement disorder, including to a lower brain region, to a pontine region, to a mesopontine region, to a globus pallidus and/or to a thalamic region of the brain.

The neurotoxin can be a modified neurotoxin, that is a neurotoxin which has at least one of its amino acids deleted, modified or replaced, as compared to a native or the modified neurotoxin can be a recombinant produced neurotoxin or a derivative or fragment thereof.

Intracranial administration of a neurotoxin according to the present invention can include the step of implantation of controlled release *botulinum* toxin system. A detailed embodiment of the present invention can be a method for treating a movement disorder by intracranial administration of a therapeutically effective amount of a *botulinum* toxin to a patient to thereby treating a symptom of a movement disorder. The movement disorders treated can include Parkinson's disease, Huntington's Chorea, progressive supranuclear palsy, Wilson's disease, Tourettes syndrome, epilepsy, chronic tremor, tics, dystonias and spasticity.

A further embodiment within the scope of the present invention can be a method for treating a movement disorder, the method comprising the steps of: selecting a neurotoxin with tremor suppressant activity; choosing an intracranial target tissue which influences a movement disorder; and; intracranially administering to the target tissue a therapeutically effective amount of the neurotoxin selected, thereby treating the movement disorder.

Thus, a method for treating a movement disorder according to the present invention can have the step of intracranial administration of a neurotoxin to a mammal, thereby alleviating a symptom of a movement disorder experienced by the mammal. Most preferably, the *botulinum* toxin used is *botulinum* toxin type A because of the high potency, ready availability and long history of clinical use of *botulinum* toxin type A to treat various disorders.

I have surprisingly found that a *botulinum* toxin, such as *botulinum* toxin type A, can be intracranially administered in amounts between about $10^{-3}$ U/kg and about 10 U/kg to alleviate a movement disorder experienced by a human patient. Preferably, the *botulinum* toxin used is intracranially administered in an amount of between about $10^{-2}$ U/kg and about 1 U/kg. More preferably, the *botulinum* toxin is administered in an amount of between about $10^{-1}$ U/kg and about 1 U/kg. Most preferably, the *botulinum* toxin is administered in an amount of between about 0.1 unit and about 5 units. Significantly, the movement disorder alleviating effect of the present disclosed methods can persist for between about 2 months to about 6 months when administration is of aqueous solution of the neurotoxin, and for up to about five years when the neurotoxin is administered as a controlled release implant.

A further preferred method within the scope of the present invention is a method for treating a movement disorder by selecting a neurotoxin with tremor suppressant activity, choosing an intracranial target tissue which influences a movement disorder; and intracranially administering to the target tissue a therapeutically effective amount of the neurotoxin selected.

Another preferred method within the scope of the present invention is a method for improving patient function, the method comprising the step of intracranially administering a neurotoxin to a patient, thereby improving patient function as determined by improvement in one or more of the factors of reduced pain, reduced time spent in bed, increased ambulation, healthier attitude and a more varied lifestyle.

DESCRIPTION

The present invention is based on the discovery that significant and long lasting relief from a variety of different movement disorders can be achieved by intracranial administration of a neurotoxin. Intracranial administration permits the blood brain barrier to be bypassed and delivers much more toxin to the brain than is possible by a systemic route of administration. Furthermore, systemic administration of a neurotoxin, such as a *botulinum* toxin, is contraindicated due to the severe complications (i.e. botulism) which can result from entry of a *botulinum* toxin into the general circulation. Additionally, since *botulinum* toxin does not penetrate the blood brain barrier to any significant extent, systemic administration of a *botulinum* toxin has no practical application to treat an intracranial target tissue.

The present invention encompasses any suitable method for intracranial administration of a neurotoxin to a selected target tissue, including injection of an aqueous solution of a neurotoxin and implantation of a controlled release system, such as a neurotoxin incorporating polymeric implant at the selected target site. Use of a controlled release implant reduces the need for repeat injections.

Intracranial implants are known. For example, brachytherapy for malignant gliomas can include stereotactically implanted, temporary, iodine-125 interstitial catheters. Scharfen. C. O., et al., *High Activity Iodine-*125 *Interstitial Implant For Gliomas*, Int. J. Radiation Oncology Biol Phys 24(4);583–591:1992. Additionally, permanent, intracranial, low dose $^{125}$I seeded catheter implants have been used to treat brain tumors. Gaspar, et al., *Permanent* $^{125}$*I Implants for Recurrent Malignant Gliomas*, Int J Radiation Oncology Biol Phys 43(5);977–982:1999. See also chapter 66, pages 577–580, Bellezza D., et al., *Stereotactic Interstitial Brachytherapy*, in Gildenberg P. L. et al., *Textbook of Stereotactic and Functional Neurosurgery*, McGraw-Hill (1998).

Furthermore, local administration of an anti cancer drug to treat malignant gliomas by interstitial chemotherapy using surgically implanted, biodegradable implants is known. For example, intracranial administration of 3-bis(chloro-ethyl)-1-nitrosourea (BCNU) (Carmustine) containing polyanhydride wafers, has found therapeutic application. Brem, H. et al., *The Safety of Interstitial Chemotherapy with BCNU-Loaded Polymer Followed by Radiation Therapy in the Treatment of Newly Diagnosed Malignant Gliomas: Phase I Trial*, J Neuro-Oncology 26:111–123:1995.

A polyanhydride polymer, GLIADEL® (Stolle R & D, Inc., Cincinnati, Ohio) a copolymer of polycarboxyphenoxypropane and sebacic acid in a ratio of 20:80 has been used to make implants, intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2–3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345;1008–1012:1995.

An implant can be prepared by mixing a desired amount of a stabilized neurotoxin (such as non-reconstituted BOTOX®) into a solution of a suitable polymer dissolved in methylene chloride, at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine* 4-*Hydroperoxycyclophosphamide and Paclitaxel From a Biodegradable Polymer Implant in the Monkey Brain*, Cancer Research 58;672–684:1998.

Diffusion of biological activity of a *botulinum* toxin within a tissue appears to be a function of dose and can be graduated. Jankovic J., et al *Therapy With Botulinum Toxin*, Marcel Dekker, Inc., (1994), page 150.

Local, intracranial delivery of a neurotoxin, such as a *botulinum* toxin, can provide a high, local therapeutic level of the toxin and can significantly prevent the occurrence of any systemic toxicity since many neurotoxins, such as the *botulinum* toxins are too large to cross the blood brain barrier. A controlled release polymer capable of long term, local delivery of a neurotoxin to an intracranial site can circumvent the restrictions imposed by systemic toxicity and the blood brain barrier, and permit effective dosing of an intracranial target tissue. A suitable implant, as set forth in co-pending U.S. patent application Ser. No. 09/587250 entitled "Neurotoxin Implant", allows the direct introduction of a chemotherapeutic agent to a brain target tissue via a controlled release polymer. The implant polymers used are preferably hydrophobic so as to protect the polymer incorporated neurotoxin from water induced decomposition until the toxin is released into the target tissue environment.

Local intracranial administration of a *botulinum* toxin, according to the present invention, by injection or implant to e.g. the cholinergic thalamus presents as a superior alternative to thalamotomy in the management of inter alia tremor associated with Parkinson's disease.

A method within the scope of the present invention includes stereotactic placement of a neurotoxin containing implant using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

Within wishing to be bound by theory, a mechanism can be proposed for the therapeutic effects of a method practiced according to the present invention. Thus, a neurotoxin, such as a *botulinum* toxin, can inhibit neuronal exocytosis of several different CNS neurotransmitters, in particular acetylcholine. It is known that cholinergic neurons are present in the thalamus. Additionally, cholinergic nuclei exist in the basal ganglia or in the basal forebrain, with protections to motor and sensory cerebral regions. Thus, target tissues for a method within the scope of the present invention can include neurotoxin induced, reversible denervation of intracranial motor areas (such as the thalamus) as well as brain cholinergic systems themselves (such as basal nuclei) which project to the intracranial motor areas. For example, injection or implantation of a neurotoxin to a cholinergically innervated thalamic nuclei (such as Vim) can result in (1) downregulation of Vim activity due to the action of the toxin upon cholinergic terminals projecting into the thalamus from basal ganglia, and; (2) attenuation of thalamic output due to the action of the toxin upon thalamic somata, both cholinergic and non-cholinergic, thereby producing a chemical thalamotomy.

Preferably, a neurotoxin used to practice a method within the scope of the present invention is a *botulinum* toxin, such as one of the serotype A, B, C, D, E, F or G *botulinum* toxins. Preferably, the *botulinum* toxin used is *botulinum* toxin type A, because of its high potency in humans, ready availability, and known use for the treatment of skeletal and smooth muscle disorders when locally administered by intramuscular injection. *Botulinum* toxin type B is a less preferred neurotoxin to use in the practice of the disclosed methods because type B is known to have a significantly lower potency and efficacy as compared, to type A, is not readily available, and has a limited history of clinical use in humans. Furthermore, the higher protein load with regard to type B can cause immunogenic reaction to occur with development of antibodies to the type B neurotoxin.

The amount of a neurotoxin selected for intracranial administration to a target tissue according to the present disclosed invention can be varied based upon criteria such as the movement disorder being treated, its severity, the extent of brain tissue involvement or to be treated, solubility characteristics of the neurotoxin toxin chosen as well as the age, sex, weight and health of the patient. For example, the extent of the area of brain tissue influenced is believed to be proportional to the volume of neurotoxin injected, while the quantity of the tremor suppressant effect is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

I have found that a neurotoxin, such as a *botulinum* toxin, can be intracranially administered according to the present disclosed methods in amounts of between about $10^{-3}$ U/kg to about 10 U/kg. A dose of about $10^{-3}$ U/kg can result in a tremor suppressant effect if delivered to a small intracranial nuclei. Intracranial administration of less than about $10^{-3}$ U/kg does not result in a significant or lasting therapeutic result. An intracranial dose of more than 10 U/kg of a neurotoxin, such as a *botulinum* toxin, poses a significant risk of denervation of sensory or desirable motor functions of neurons adjacent to the target.

A preferred range for intracranial administration of a *botulinum* toxin, such as *botulinum* toxin type A, so as to achieve a tremor suppressant effect in the patient treated is from about $10^{-2}$ /kg to about 1 U/kg. Less than about $10^{-2}$ U/kg can result in a relatively minor, though still observable, tremor suppressant effect. A more preferred range for intracranial administration of a *botulinum* toxin, such as *botulinum* toxin type A, so as to achieve an antinociceptive effect in the patient treated is from about $10^{-}1$ U/kg to about 1 U/kg. Less than about $10^{-1}$ U/kg can result in the desired therapeutic effect being of less than the optimal or longest possible duration.. A most preferred range for intracranial administration of a *botulinum* toxin, such as *botulinum* toxin type A, so as to achieve a desired tremor suppressant effect in the patient treated is from about 0.1 units to about 100 units. Intracranial administration of a *botulinum* toxin, such as *botulinum* toxin type A, in this preferred range can provide dramatic therapeutic success.

The present invention includes within its scope the use of any neurotoxin which has a long duration tremor suppressant effect when locally applied intracranially to the patient. For example, neurotoxins made by any of the species of the toxin producing Clostridium bacteria, such as *Clostridium botulinum, Clostridium butyricum*, and *Clostridium beratti* can be used or adapted for use in the methods of the present invention. Additionally, all of the *botulinum* serotypes A, B, $C_1$, D, E , F and G can be advantageously used in the practice of the present invention, although type A is the most preferred and type B the least preferred serotype, as explained above. Practice of the present invention can provide a tremor suppressant effect, per injection, for 3 months or longer in humans.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting treatment of a movement disorder can be achieved by intracranial administration of a neurotoxin to an afflicted patient. In its most preferred embodiment, the present invention is practiced by intracranial injection or implantation of *botulinum* toxin type A.

The present invention does include within its scope: (a) neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made.

*Botulinum* toxins for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as albumin. The lyophilized material can be reconstituted with saline or water.

EXAMPLES

The following examples set forth specific methods encompassed by the present invention to treat a movement disorder and are not intended to limit the scope of the invention.

Example 1

Intracranial Target Tissue Localization and Methodology

Stereotactic procedures can be used for precise intracranial administration of neurotoxin in aqueous form or as an implant to desired target tissue. Thus, intracranial administration of a neurotoxin to treat a drug resistant tremor (i.e. a resting tremor, such as can occur in Parkinson's disease, or an action tremor, such as essential tremor), multiple sclerosis tremors, post traumatic tremors, post hemiplegic tremors (post stroke spasticity), tremors associated with neuropathy, writing tremors and epilepsy can be carried out as follows.

A preliminary MRI scan of the patient can be carried out to obtain the length of the anterior commissure-posterior commissure line and its orientation to external bony landmarks. The base of the frame can then be aligned to the plane of the anterior commissure-posterior commissure line. CT guidance is used and can be supplemented with ventriculography. The posterior commissure can be visualized on 2-mm CT slices and used as a reference point. Where the target injection site is the basal part of the ventral intermedius nucleus of the ventrolateral thalamus, average coordinates are 6.5 mm anterior to the posterior commissure, 11 mm lateral to the third ventricular wall and 2 mm above the anterior commissure-posterior commissure line. This location is not expected to encroach on the sensory thalamus or on a subthalamic region.

Physiological corroboration of target tissue localization can be by use of high and low frequency stimulation through an electrode accompanying or incorporated into the long needle syringe used. A thermistor electrode 1.6 mm in diameter with a 2 mm exposed tip can be used (Radionics, Burlington, Mass.). With electrode high frequency stimulation (75 Hz) paraesthetic responses can be elicited in the forearm and hand at 0.5–1.0 V using a Radionics lesion generator (Radionics Radiofrequency Lesion Generator Model RFG3AV). At low frequency (5 Hz) activation or disruption of tremor in the affected limb occurred at 2–3 V. With the methods of the present invention, the electrode is not used to create a lesion. Following confirmation of target tissue localization, a neurotoxin can be injected, thereby causing a reversible, chemical thalamotomy. A typical injection is the desired number of units (i.e. about 0.1 to about 5 units of a *botulinum* toxin type A complex in about 0.1 ml to about 0.5 ml of water or saline. A low injection volume can be uses to minimize toxin diffusion away from target. Typically, the neurotransmitter release inhibition effect can be expected to wear off within about 2–4 months. Thus, an alternate neurotoxin format, neurotoxin incorporated within a polymeric implant, can be used to provide controlled, continuous release of therapeutic amount of the toxin at the desired location over a prolonged period.(i.e. from about 1 year to about 6 years), thereby obviating the need for repeated toxin injections.

Several methods can be used for stereotactically guided injection of a neurotoxin to various intracranial targets, such as the subthalamic nucleus (STN) for treatment of Parkinson's disease (Parkinson's disease). Thus a stereotactic magnetic resonance (MRI) method relying on three-dimensional (3D) T1-weighted images for surgical planning and multiplanar T2-weighted images for direct visualization of the STN, coupled with electrophysiological recording and injection guidance for unilateral or bilateral STN injection can be used. See e.g. Bejjani, B. P., et al., *Bilateral Subthalamic Stimulation for Parkinson's Disease by Using Three-Dimensional Stereotactic Magnetic Resonance Imaging and Electrophysiological Guidance*, J Neurosurg 92(4) ;615–25:2000. The STNs can be visualized as 3D ovoid biconvex hypointense structures located in the upper mesencephalon. The coordinates of the centers of the STNs can be determined with reference to the patient's anterior commissure-posterior commissure line by using as a landmark, the anterior border of the red nucleus.

Electrophysiological monitoring through several parallel tracks can be performed simultaneously to define the functional target accurately. Microelectrode recording can identify high-frequency, spontaneous, movement-related activity and tremor-related cells within the STNs. Neurotoxin injection into the STN can improve contralateral rigidity and akinesia and suppress tremor when present. The central track, which is directed at the predetermined target by using MRI imaging, can be selected for neurotoxin injection. No surgical complications are expected. The patient can show significantly improved parkinsonian motor disability in the "off" and "on" medication states and use of antiparkinsonian drug treatment can be dramatically reduced as is the severity of levodopa-induced dyskinesias and motor fluctuations.

Computer-aided atlas-based functional neurosurgery methodology can be used to accurately and precisely inject the desired neurotoxin or implant a neurotoxin controlled release implant. Such methodologies permit three-dimensional display and real-time manipulation of cerebral structures. Neurosurgical planning with mutually preregistered multiple brain atlases in all three orthogonal orientations is therefore possible and permits increased accuracy of target definition for neurotoxin injection or implantation, reduced time of the surgical procedure by decreasing the number of tracts, and facilitates planning of more sophisticated trajectories. See e.g. Nowinski W. L. et al., *Computer-Aided Stereotactic Functional Neurosurgery Enhanced by the Use of the Multiple Brain Atlas Database*, IEEE Trans Med Imaging 19(1);62–69:2000.

Example 2

Treatment of Parkinson's Disease with Botulinum Toxin Type A

A 64 year old right-handed male presents with pronounced tremor of the extremities, bradykinesia, rigidity and postural changes such that he frequently falls. A prominent pill rolling tremor is noted in his right hand. Stroke is ruled out and it is noted that the symptoms are worse on his right side. Diagnosis of Parkinson's disease is made. Using CAT scan or MRI assisted stereotaxis, as set forth in Example 1 above, 2 units of a *botulinum* toxin type A (such as BOTOX® or about 8 units of DYSPORT®) is injected into the left side of the globus pallidus. The patient is discharged within 48 hours and with a few (1–7) days enjoys significant improvement of the parkinsonian motor symptoms more clearly on the right, but also on his left side. His dyskinesias almost completely disappear. The motor disorder symptoms of Parkinson's disease remain significantly alleviated for between about 2 to about 6 months. For extended therapeutic relief, one or more polymeric implants incorporating a suitable quantity of a *botulinum* toxin type A can be placed at the target tissue site.

Example 3

Treatment of Parkinson's Disease with *botulinum* Toxin Type B

A 68 year left handed male presents with pronounced tremor of the extremities. bradykinesia, rigidity and postural changes such that he frequently falls. A prominent pill rolling tremor is noted on his left side. Stroke is ruled out and it is noted that the symptoms are worse on his left side. Diagnosis of Parkinson's disease is made. Using CAT scan or MRI assisted stereotaxis, as set forth in Example 1 above, from 10 to about 50 units of a *botulinum* toxin type B preparation (such as NEUROBLOC® or INERVATE™) is injected into the right side of the globus pallidus. The patient is discharged within 48 hours and with a few (1–7) days enjoys significant improvement of the parkinsonian motor symptoms more clearly on the left, but also on his right side. His dyskinesias almost completely disappear. The motor disorder symptoms of Parkinson's disease remain significantly alleviated for between about 2 to about 6 months. For extended therapeutic relief, one or more polymeric implants incorporating a suitable quantity of a *botulinum* toxin type B can be placed at the target tissue site.

Example 4

Treatment of Parkinson's Disease with *botulinum* Toxin Types $C_1$–G

A female aged 71 is admitted with uncontrollable and frequent tremor. From 0.1 to 100 units of a *botulinum* toxin type $C_1$, D, E, F or G is injected unilaterally into the ventrolateral thalamus for the disabling tremors. CAT scan or MRI assisted stereotaxis, as set forth in Example 1 above, supplemented by ventriculography is used. The patient is discharged within 48 hours and with a few (1–7) days enjoys significant remission of tremors which remain significantly alleviated for between about 2 to about 6 months. For extended therapeutic relief, one or more polymeric implants incorporating a suitable quantity of a *botulinum* toxin type $C_1$, D, E, F or G can be placed at the target tissue site.

Example 5

Treatment of Dystonia with *botulinum* Toxin Type A

A 16 year old male child with severe, incapacitating dystonia, secondary to cranial trauma, affecting the proximal limb muscles is a candidate for unilateral thalamotomy on the left side, bilateral thalamotomy carrying a high risk of iatrogenic dysarthria and pseudubulbar effects. The patient has failed to respond or has become unresponsive to transcutaneous nerve stimulation, feedback display of the EMG and anticholinergics. The dystonia is relatively stable, the patient is sufficiently fit to withstand surgery and is significantly disabled with distal phasic and tonic limb dystonia.

A suitable stereotactic frame can be applied to the head with local anesthetic and ventriculography and stereotactic MRI can be performed. The stereotactic coordinates of the anterior commissure (AC) and the posterior commissure (PC) can be determined by using the computer software in the scanner. PC based software can be used to redraw the sagittal brain maps from the Schaltenbrand and Bailey and Schaltenbrand and Wahren atlases, stretched or shrunk as needed to the AC-PC distance of the patient and ruled in stereotactic coordinates for the actual application of the frame to the patient's head. The target sites are selected, their coordinates are read off and appropriate frame settings are made. A burr hole or twist-drill hole can be made at or rostral to the coronal suture in the same sagittal plane as the target. This can facilitate plotting the physiological data used for target corroboration since the electrode trajectories traverse a single sagittal plane. The ventrocaudal nucleus of the thalamus (Vc) can be selected as a physiological landmark, lying 15 mm from the midline. The Vc can be easily recognized by recording individual tactile cells within it with their discrete receptive fields or by inducing paresthesias with stimulation in discreet projected fields.

A microelectrode recording needle (such a used for single fiber electromyographic recording having an approximately 25 micron diameter recording electrode) can be located within the bore of a microsyringe and is advanced toward the expected tactile representation of the fingers in the Vc and continuous recording is carried out to search for identifiable neurons. Microstimulation can be performed every millimeter, beginning about 10 mm above and extending to a variable distance below the target. If the first microelectrode trajectory enters, for example, the tactile representation of the lips of a patient with upper limb dystonia, a second trajectory can be carried out 2 mm more lateral. Upon encountering lower limb responses, the next trajectory can be made 2 mm more medial. Once the tactile representation of the hand is found, the next trajectory can be made 2 mm rostral to it, where recording reveals kinesthetic neurons that respond to bending of specific contralateral joints or pressure on specific contralateral sites. If dystonia is confined to the leg, the process described above can be aimed at the thalamic representation for the leg.

Upon microstimulation localization of the stereotactically-MRI guided recording/stimulating needle electrode to the target, a neurotoxin implant can be injected. The implant can comprise a neurotoxin, such as a of *botulinum* toxin type A, incorporated within biodegradable polymeric microspheres or a biodegradable pellet, either implant format containing about 20 total units (about 1 ng) of the toxin with implant characteristics of continuous release over a period of at least about four years of a therapeutic level of the toxin at point of the implant release site and for a radius of about 2–3 mm on each side o the target site. The implant can release about 1 unit of toxin essentially immediately and further amounts of about one unit cumulatively over subsequent 2–4 months periods.

The patient's dystonic contractions can subside almost immediately, and can remain substantially alleviated for between about 2 months to about 6 months per toxin injection or for between about 1 to 5 years depending upon the particular release characteristics of the implant polymer and the quantity of neurotoxin loaded therein.

Example 6

Treatment of Dystonia with Botulinum Toxin Types B–G

The patient of example 5 above can be equivalently treated using the same protocol and approach to target with between about 1 unit and about 1000 units of a *botulinum* toxin type B, $C_1$, D, E, F or G in aqueous solution or in the form of a suitable neurotoxin implant. with such a treatment, the dystonic contractions subside within 1–7 days, and remain substantially alleviated for between about 2–6 months per toxin injection or for between about 1 to 5 years depending upon the particular release characteristics of the implant polymer and the quantity of neurotoxin loaded therein.

Example 7

Treatment of Tremor with *botulinum* Toxin Type A

A 44 year old male presents with severe incapacitating tremor of three years duration which disrupts his activities of daily living. There is also asymmetry of the motor symptoms between the two side of the body and levodopa has induced dyskinesia in the extremities. Tremor cells are identified by stereotactic examination of the effect upon the tremor by electrical stimulation of the proposed target cell. The effect of stimulation is noted to inhibit the tremor. Stereotactic guided (as in Example 1) implant placement can be made at a site about 14 to 15 mm from the midline and 2–3 mm above the AC-PC line in the middle of kinesthetic and/or voluntary tremor cells. The target site can be the VL or Vi.

The implant can be either an aqueous solution of *botulinum* toxin type A incorporated within biodegradable polymeric microspheres or *botulinum* toxin type A biodegradable pellet, either implant format containing about 20 total units (about 1 ng) of the toxin with implant characteristics of continuous release over a period of at least about four years of a therapeutic level of the toxin at point of the implant release site and in about 2–3 mm on each side. The implant can release about 1 unit of toxin essentially immediately and further amounts of about one unit cumulatively over subsequent 2–4 months periods.

The patient's tremors can subside within 1–7 days, and can remain substantially alleviated for between about 2 months to about 6 months per toxin injection or for between about 1 to 5 years depending upon the particular release characteristics of the implant polymer and the quantity of neurotoxin loaded therein. Notably, there can be significant attenuation of distal limb movements, both phasic and tonic on the right side.

Example 8

Treatment of Tremor with *botulinum* Toxin Types B–G

The patient of example 7 above can be equivalently treated using the same protocol and approach to target with between about 1 unit and about 1000 units of a *botulinum* toxin type B, $C_1$, D, E, F or G in aqueous solution or in the form of a suitable neurotoxin implant. with such a treatment, the tremors can subside within 1–7 days, and can remain substantially alleviated for between about 2–6 months per toxin injection or for between about 1 to 5 years depending upon the particular release characteristics of the implant polymer and the quantity of neurotoxin loaded therein.

Example 9

Treatment of Epilepsy with *botulinum* Toxin Type A

A right handed, female patient age 22 presents with a history of epilepsy. Based upon MRI and a study of EEG recording, a diagnosis of temporal lobe epilepsy is made. An implant which provides about 5–50 units of a neurotoxin (such as a *botulinum* toxin type A) can be inserted at the anterior part of the temporal lobe, 5–6 cm from the tip of the lobe along the middle temporal gyrus with a unilateral approach to the nondominant, left hemisphere. The epileptic seizures can be substantially reduced within about 1–7 days, and can remain substantially alleviated for between about 2 months to about 6 months per toxin injection or for between about 1 to 5 years depending upon the particular release characteristics of the implant polymer and the quantity of neurotoxin loaded therein.

Example 10

Treatment of Epilepsy with *botulinum* Toxin Types B–G

The patient of example 9 above can be equivalently treated using the same protocol and approach to target with between about 1 unit and about 1000 units of a *botulinumn* toxin type B, $C_1$, D, E, F or G in aqueous solution or in the form of a suitable neurotoxin implant. with such a treatment, the epileptic seizures can subside within 1–7 days, and can remain substantially alleviated for between about 2–6 months per toxin injection or for between about 1 to 5 years depending upon the particular release characteristics of the implant polymer and the quantity of neurotoxin loaded therein.

It is concluded that neurotoxin injection or implantation of a controlled release neurotoxin implant according to the methods of the present invention, with the aid of 3D MR imaging and electrophysiological guidance, can be a safe and effective therapy for patients suffering from various movement disorders, such as severe, advanced levodopa-responsive Parkinson's disease. Suitable patients include those who have become largely if not entirely refractory to chemotherapy, typically oral L-dopa, prior to intracranial neurotoxin administration as set forth herein.

A method according to the present invention can also be used diverse movement disorders, including essential tremor, multiple sclerosis related tremors, post traumatic tremors, post hemiplegic tremors, parkinsonian tremors and epilepsy.

An intracranial neurotoxin administration method for treating a movement disorder according to the invention disclosed herein for has many benefits and advantages, including the following:

1. the symptoms of a movement disorder can be dramatically reduced.
2. the symptoms of a movement disorder can be reduced for from about two to about four months per injection of neurotoxin and for from about one year to about five years upon use of a controlled release neurotoxin implant.
3. the injected or implanted neurotoxin exerts an intracranial target tissue site specific tremor suppressant effect.

4. the injected or implanted neurotoxin shows little or no tendency to diffuse or to be transported away from the intracranial injection or implantation site.
5. few or no significant undesirable side effects occur from intracranial injection or implantation of the neurotoxin.
6. the amount of neurotoxin injected intracranially can be considerably less than the amount of the same neurotoxin required by other routes of administration (i.e. intramuscular, intrasphincter, oral or parenteral) to achieve a comparable tremor suppressant effect.
7. the tremor suppressant effects of the present methods can result in the desirable side effects of greater patient mobility, a more positive attitude, and an improved quality of life.
8. high, therapeutic doses of a neurotoxin can be delivered to an intracranial target tissue over a prolonged period without systemic toxicity.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes intracranial administration methods wherein two or more neurotoxins, such as two or more *botulinum* toxins, are administered concurrently or consecutively. For example, *botulinum* toxin type A can be administered intracranially until a loss of clinical response or neutralizing antibodies develop, followed by administration of *botulinum* toxin type B. Alternately, a combination of any two or more of the *botulinum* serotypes A–G can be intracranially administered to control the onset and duration of the desired therapeutic result. Furthermore, non-neurotoxin compounds can be intracranially administered prior to, concurrently with or subsequent to administration of the neurotoxin to proved adjunct effect such as enhanced or a more rapid onset of tremor suppression before the neurotoxin, such as a *botulinum* toxin, begins to exert its more long lasting tremor suppressant effect.

My invention also includes within its scope the use of a neurotoxin, such as a *botulinum* toxin, in the preparation of a medicament for the treatment of a movement disorder, by intracranial administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for temporary reduction of a dyskinesia of Parkinson's disease, the method comprising the step of intracranial administration of a *botulinum* toxin into a globus palladius or into a ventrolateral thalamus, thereby reducing a dyskinesia of Parkinson's disease.

2. The method of claim 1, wherein the *botulinum* toxin is selected from the group consisting of *botulinum* toxin types A, B, $C_1$, D, E, F and G.

3. The method of claim 1, wherein the *botulinum* toxin is *botulinum* toxin type A.

4. The method of claim 1, wherein the *botulinum* toxin is administered in an amount of between about $10^{-3}$ U/kg and 10 U/kg.

5. The method of claim 1, wherein the reduction of a dyskinesia of Parkinson's disease persists for between about 1 month and about 5 years.

6. The method of claim 1, wherein the *botulinum* toxin is a modified botulinum toxin.

7. The method of claim 6, wherein the modified *botulinum* toxin has at least one of its amino acids deleted, modified or replaced, as compared to a native botulinum toxin.

8. The method of claim 6, wherein the modified *botulinum* toxin is a recombinant produced *botulinum* toxin or a derivative or fragment thereof.

9. The method of claim 1, wherein the intracranial administration step comprises implantation of a controlled release *botulinum* toxin system.

10. A method for temporary reduction of a dyskinesia of Parkinson's disease, the method comprising the step of intracranial administration of a therapeutically effective amount of a *botulinum* toxin type A into the globus palladius or into the ventrolateral thalamus, thereby reducing a dyskinesia of Parkinson's disease.

11. The method of claim 10, wherein the reduction of a dyskinesia persists for between about 1 month and about 5 years.

12. A method for reducing a dyskinesia of Parkinson's disease, the method comprising the step of intracranial administration of a *botulinum* toxin into a globus palladius nucleus or into a ventrolateral thalamus nucleus of a patient, thereby reducing a dyskinesia of the patient for a period of time of between about 1 month and about 5 years.

13. The method of claim 12, wherein the *botulinum* toxin is selected from the group consisting of *botulinum* toxin types A, B, $C_1$, D, E, F and G.

14. A method for temporary reduction of a tremor of Parkinson's disease, the method comprising the step of intracranial administration of a *botulinum* toxin into a globus palladius or into a ventrolateral thalamus, thereby reducing a tremor of Parkinson's disease.

15. The method of claim 14, wherein the *botulinum* toxin is selected from the group consisting of *botulinum* toxin types A, B, $C_1$, D, E, F and G.

16. The method of claim 14, wherein the *botulinum* toxin is *botulinum* toxin type A.

17. The method of claim 14, wherein the reduction of a tremor of Parkinson's disease persists for between about 1 month and about 5 years.

* * * * *